US010762764B1

(12) United States Patent
King

(10) Patent No.: US 10,762,764 B1
(45) Date of Patent: Sep. 1, 2020

(54) BIOMETRIC MONITORING SYSTEM

(71) Applicant: Tomanika King, Los Angeles, CA (US)

(72) Inventor: Tomanika King, Los Angeles, CA (US)

( * ) Notice: Subject to any disclaimer, the term of this patent is extended or adjusted under 35 U.S.C. 154(b) by 0 days.

(21) Appl. No.: 16/679,238

(22) Filed: Nov. 10, 2019

(51) Int. Cl.
*G08B 1/08* (2006.01)
*G08B 21/18* (2006.01)
(Continued)

(52) U.S. Cl.
CPC .......... *G08B 21/182* (2013.01); *A61B 5/0077* (2013.01); *A61B 5/01* (2013.01); *A61B 5/02055* (2013.01); *A61B 5/14542* (2013.01); *A61B 5/4266* (2013.01); *A61B 5/4362* (2013.01); *A61B 5/6823* (2013.01); *A61B 5/6844* (2013.01); *A61B 5/742* (2013.01); *A61B 5/7405* (2013.01); *A61B 5/746* (2013.01); *A61B 5/747* (2013.01); *A61B 5/7455* (2013.01); *G08B 7/06* (2013.01); *A61B 5/021* (2013.01); *A61B 5/024* (2013.01); *A61B 2503/02* (2013.01);
(Continued)

(58) Field of Classification Search
CPC ...... G08B 21/182; G08B 7/06; A61B 5/0077; A61B 5/01; A61B 5/02055; A61B 5/14542; A61B 5/4266; A61B 5/4362; A61B 5/6823; A61B 5/6844; A61B 5/7405; A61B 5/742; A61B 5/7455; A61B 5/746; A61B 5/747; A61B 5/021; A61B 5/024; A61B 2503/02; A61B 2560/0209; A61B 2560/0214; A61B 2562/0204; A61B 2562/0219
USPC ..................................................... 340/539.22
See application file for complete search history.

(56) References Cited

U.S. PATENT DOCUMENTS 9,811,818 B1 * 11/2017 Xing .................. A61B 10/0051
10,621,164 B1 * 4/2020 Kain .................. G06F 16/2365
(Continued)

*Primary Examiner* — Kerri L McNally
*Assistant Examiner* — Thang D Tran

(57) ABSTRACT

A biometric monitoring system is provided comprising one or more first biometric monitoring devices each comprising a first plurality of biometric sensors, a display screen, a first band body and a first securement mechanism coupling the first band body around a first user's body part. The system further comprises a second biometric monitoring device comprising a second plurality of biometric sensors, a second band body and a second securement mechanism coupling the second band body around a pregnant user's back, sides and midriff. The one or more first biometric monitoring devices are in wireless communication with one or more remote electronic devices and the one or more second biometric monitoring devices, and the one or more second biometric monitoring devices are in wireless communication with the one or more remote electronic devices. The one or more remote electronic devices each comprise a graphical user interface allowing a remote user to set one or more threshold values for each of the first and second plurality of biometric sensors. When the first or second biometric monitoring devices determine that the one or more threshold values have been met, two or more actions are triggered including alerting emergency services, the first user, the pregnant user and/or the one or more remote users in substantially real-time via audio, tactile and/or video communication.

18 Claims, 2 Drawing Sheets

104

106

102

100

(51) Int. Cl.

| | |
|---|---|
| ***A61B 5/00*** | (2006.01) |
| ***A61B 5/0205*** | (2006.01) |
| ***A61B 5/01*** | (2006.01) |
| ***A61B 5/145*** | (2006.01) |
| ***G08B 7/06*** | (2006.01) |
| *A61B 5/024* | (2006.01) |
| *A61B 5/021* | (2006.01) |

(52) U.S. Cl.

CPC ................. *A61B 2560/0209* (2013.01); *A61B 2560/0214* (2013.01); *A61B 2562/0204* (2013.01); *A61B 2562/0219* (2013.01)

(56) References Cited

U.S. PATENT DOCUMENTS

| | | | | |
|---|---|---|---|---|
| 2014/0228653 | A1* | 8/2014 | Kiraly | A61B 5/4362 600/301 |
| 2015/0137994 | A1* | 5/2015 | Rahman | H04W 4/50 340/870.07 |
| 2015/0287338 | A1* | 10/2015 | Wells | G09B 19/003 702/19 |
| 2016/0000374 | A1* | 1/2016 | Dandekar | A61B 5/0476 600/301 |
| 2016/0128594 | A1* | 5/2016 | Amir | A61B 5/02411 600/382 |
| 2016/0262687 | A1* | 9/2016 | Vaidyanathan | A61B 5/1123 |
| 2016/0310062 | A1* | 10/2016 | Larson | A61B 5/742 |
| 2016/0324442 | A1* | 11/2016 | Zdeblick | A61B 5/073 |
| 2017/0035367 | A1* | 2/2017 | Reich | A61B 5/746 |
| 2017/0156594 | A1* | 6/2017 | Stivoric | A61B 5/7275 |
| 2017/0196514 | A1* | 7/2017 | Moltani | A61B 5/6804 |
| 2017/0224268 | A1* | 8/2017 | Altini | A61B 5/4362 |
| 2017/0258436 | A1* | 9/2017 | Kjæer Thing Riknagel | A61B 7/04 |
| 2017/0281087 | A1* | 10/2017 | Workman | A61B 5/4362 |
| 2017/0340209 | A1* | 11/2017 | Klaassen | A61B 5/11 |
| 2018/0000405 | A1* | 1/2018 | Penders | A61B 5/14539 |
| 2018/0036534 | A1* | 2/2018 | Shin | A61B 5/0022 |
| 2018/0225271 | A1* | 8/2018 | Bellamy | G06F 16/345 |
| 2018/0353085 | A1* | 12/2018 | Olivero | A61B 5/6831 |
| 2018/0368753 | A1* | 12/2018 | Yin | A61B 5/4362 |
| 2019/0000384 | A1* | 1/2019 | Gupta | A61B 5/6804 |
| 2019/0192064 | A1* | 6/2019 | Cantor | A61B 5/01 |
| 2019/0206538 | A1* | 7/2019 | Xing | A61B 5/4848 |
| 2019/0209777 | A1* | 7/2019 | O'Connell | A61B 5/14532 |
| 2019/0261874 | A1* | 8/2019 | Berg | B29C 45/0001 |
| 2019/0320944 | A1* | 10/2019 | Vaidyanathan | A61B 5/4519 |
| 2020/0128670 | A1* | 4/2020 | Chong Rodriguez | H05K 1/145 |
| 2020/0196958 | A1* | 6/2020 | Penders | A61B 5/7267 |

* cited by examiner

BIOMETRIC MONITORING SYSTEM

BACKGROUND OF THE INVENTION

One of the most difficult challenges for parents is maintaining a watchful eye over the safety of their children, whether unborn, infants, toddlers, preteens or teenaged. Generally, parents rely upon existing family members, friends, neighbors and the like to assist in this task. However, situations inevitably arise where the parents, family members, friends, neighbors etc. cannot adequately care for or monitor the well-being of such children. Typical situations include a pregnant mother who does not have the medical knowledge to monitor the well-being of the unborn child, one or more infant or toddler children being watched by a third party such as a babysitter or daycare service, one or more preteen or teenaged children playing outside unattended and the like.

Without the ability to adequately watch such children, immense stress and anxiety may be placed upon the parent as a cause of not knowing the safety status of their children. Consequently, parents may be apprehensive about letting their children go under the care of a babysitter, daycare service, preschool and the like, to independently play outside with friends or to socialize with friends after school and the like which potentially limits the social and physical development of the child. Further, the stress and anxiety of the parents may lead to a lower quality of life for the parents and lower the quality of the relationship between parent and child.

To avoid such situations, a means of remotely monitoring such children would be advantageous. In the context of pregnant mothers, a wearable device worn by the mother monitoring the biometrics of both the unborn child and the pregnant mother would be advantageous. In the context of other children, a wearable device worn by the child configured to monitor via biometric and location data the physiological safety of the children would be advantageous. Further, the ability to communicate and display such biometric and location data in substantially real-time would be advantageous.

SUMMARY

In some embodiments, a biometric monitoring system is provided, comprising one or more first biometric monitoring devices each comprising a first plurality of biometric sensors, a display screen, a first band body and a first securement mechanism coupling the first band body around a first user's body part, wherein the first band body and display screen structurally support the first plurality of biometric sensors and wherein the first band body comprises a substantially annular shape; and a second biometric monitoring device comprising a second plurality of biometric sensors, a second band body and a second securement mechanism coupling the second band body around a pregnant user's back, sides and midriff, wherein the second band body structurally supports one or more of the second plurality of biometric sensors and wherein the second band body comprises a substantially annular shape having a vertical height reaching a maximum at the pregnant user's back and tapering to a minimum at the pregnant user's midriff, wherein the one or more first biometric monitoring devices are in wireless communication with one or more remote electronic devices and the one or more second biometric monitoring devices, and the one or more second biometric monitoring devices are in wireless communication with the one or more remote electronic devices, wherein the one or more remote electronic devices each comprising a graphical user interface allowing a remote user to set one or more threshold values for each of the first and second plurality of biometric sensors such that, when the first or second biometric monitoring devices determine that the one or more threshold values have been met, two or more actions are triggered, wherein the two or more actions triggered comprise alerting emergency services, the first user, the pregnant user and/or the one or more remote users in substantially real-time via audio, tactile and/or video communication.

In some embodiments, the first plurality of biometric sensors comprise two or more selected from the group consisting of: location tracking sensors, cameras, microphones, heart rate monitoring sensors, blood oxygen sensors, environmental and dermal temperature sensors, blood pressure sensors, securement mechanism status sensors, accelerometers and any combination thereof.

In some embodiments, the first plurality of biometric sensors monitor substantially in real-time two or more parameters selected from the group consisting of: first user location, live video feed, live audio feed, heart rate, blood oxygen level, temperature, blood pressure, securement mechanism status, acceleration and any combination thereof.

In some embodiments, the second plurality of biometric sensors comprise two or more selected from the group consisting of: ultrasound transceivers, heart rate monitoring sensors, blood oxygen sensors, dermal temperature sensors, blood pressure sensors, sweat analysis sensors, accelerometers and any combination thereof.

In some embodiments, the second plurality of biometric sensors monitor substantially in real-time two or more parameters selected from the group consisting of: fetal position, fetal orientation, heart rate, blood oxygen level, temperature, blood pressure, sweat composition, acceleration and any combination thereof.

In some embodiments, the one or more threshold values determine any one of the following: when a fetus of the pregnant user moves or orients itself outside a threshold position or orientation, when the pregnant user is starting labor, when the pregnant user or their fetus is experiencing malnutrition, when the fetus of the pregnant user is not receiving enough oxygen, when an accelerometer records a high-impact event or any combination thereof.

In some embodiments, the second biometric monitoring device comprises a third band body coupled to the second band body at two locations, the two locations are disposed adjacent the pregnant user's womb and the third band body is disposed over a top of the pregnant user's womb.

In some embodiments, the second biometric monitoring device comprises a rechargeable power source operably coupled to a switch configured to selectively place the second biometric monitoring device in an ON state and an OFF state and the rechargeable power source is operably coupled to a processing control unit configured to place the switch into the OFF state after a predetermined period of time of inactivity.

In some embodiments, the second biometric monitoring device comprises one or more processing control units configured to selectively place one or more of the second plurality of biometric sensors in an ON state and an OFF state and the one or more processing control units place one or more of the second plurality of biometric sensors into the OFF state after a predetermined period of time of inactivity.

In some embodiments, a biometric monitoring system is provided, comprising one or more first biometric monitoring devices each comprising a first plurality of biometric sensors, a display screen, a first band body and a first securement mechanism coupling the first band body around a first user's body part, wherein the first band body comprises a substantially annular shape; and a second biometric monitoring device comprising a second plurality of biometric sensors, a second band body and a second securement mechanism coupling the second band body around a pregnant user's back, sides and midriff, wherein the second band body structurally supports one or more of the second plurality of biometric sensors and wherein the second band body comprises a substantially annular shape having a vertical height reaching a maximum at the pregnant user's back and tapering to a minimum at the pregnant user's midriff, wherein the second biometric monitoring device comprises one or more processing control units configured to selectively place one or more of the second plurality of biometric sensors in an ON state and an OFF state and wherein the one or more processing control units place one or more of the second plurality of biometric sensors into the OFF state after a predetermined period of time irregardless of the pregnant user's activity to prevent electromagnetic exposure to a pregnant user's fetus, wherein the one or more first biometric monitoring devices are in wireless communication with one or more remote electronic devices and the one or more second biometric monitoring devices, and the one or more second biometric monitoring devices are in wireless communication with the one or more remote electronic devices, wherein the one or more remote electronic devices each comprising a graphical user interface allowing a remote user to set one or more threshold values for each of the first and second plurality of biometric sensors such that, when the first or second biometric monitoring devices determine that the one or more threshold values have been met, two or more actions are triggered, wherein the two or more actions triggered comprise alerting emergency services, the first user, the pregnant user and/or the one or more remote users in substantially real-time via audio, tactile and/or video communication.

In some embodiments, a computer-implemented method of operating a biometric monitoring system comprising one or more processing control units executing software stored in machine-readable memory to perform actions is provided comprising: communicating electronic data between one or more first biometric monitoring devices, a second biometric monitoring device and one or more remote electronic devices, wherein the one or more first biometric monitoring devices each comprising a first plurality of biometric sensors, a display screen, a first band body and a first securement mechanism coupling the first band body around a first user's body part, wherein the first band body comprises a substantially annular shape, wherein the second biometric monitoring device comprising a second plurality of biometric sensors, a second band body and a second securement mechanism coupling the second band body around a pregnant user's back, sides and midriff, wherein the second band body structurally supports one or more of the second plurality of biometric sensors and wherein the second band body comprises a substantially annular shape having a vertical height reaching a maximum at the pregnant user's back and tapering to a minimum at the pregnant user's midriff; setting, via a graphical user interface of the one or more remote electronic devices, a plurality of threshold values associated with the first and second plurality of biometric sensors; iteratively comparing the plurality of threshold values against a plurality of parameters measured by the first and second plurality of biometric sensors; and determining whether the plurality of parameters meet or exceed the plurality of threshold values, wherein, in response to determining that the plurality of threshold values have been met or exceeded, two or more actions occur, wherein the two or more actions occurring comprise alerting emergency services, the first user, the pregnant user and/or the one or more remote users in substantially real-time via audio, tactile and/or video communication.

DETAILED DESCRIPTION OF THE INVENTION

Before describing the present invention in detail, it is to be understood that the invention is not limited to any one of the particular embodiments, which of course may vary. It is also to be understood that the terminology used herein is for the purpose of describing particular embodiments only, and therefore is not necessarily intended to be limiting. As used in this specification and the appended claims, terms in the singular and the singular forms "a," "an," and "the" include plural referents unless the context clearly dictates otherwise. Thus, for example, reference to "a biometric monitoring device" also includes a plurality of biometric monitoring devices, and the like.

Figure 1:
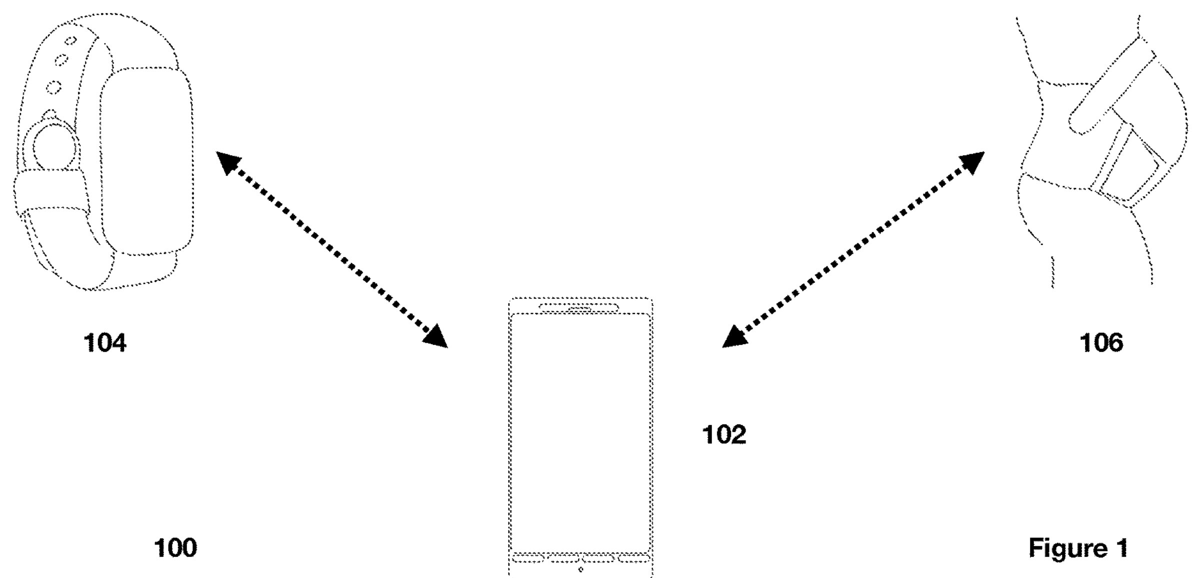
FIG. 1 is an overview of a biometric monitoring system in accordance with some embodiments of the present invention.

Exemplary embodiments of the present invention are illustrated in the accompanying figures. As shown in FIG. 1, a biometric monitoring system 100 is provided. The system comprises first and second biometric monitoring devices 104, 106 in wireless communication with one or more remote electronic devices 102. While first and second biometric monitoring devices 104, 106 are shown in FIG. 1, it is to be understood that a plurality of first biometric monitoring devices 104 and a plurality of second biometric monitoring devices 106 may be utilized in wireless communication with the one or more remote electronic devices 102. Each of the one or more remote devices 102 may be a remote server, a personal electronic device, other electronic device having a graphical user interface or any combination thereof.

Figure 2:
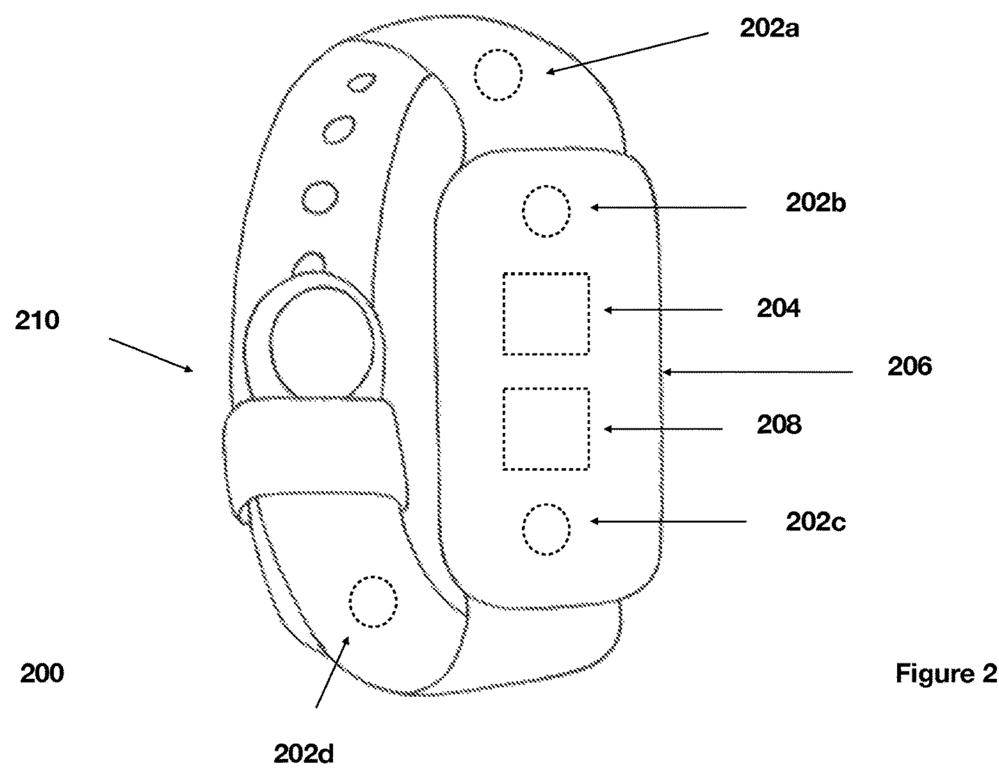
FIG. 2 is a detailed view of a first biometric monitoring device in accordance with some embodiments of the present invention.

As shown in FIG. 2, the first biometric monitoring device 200 may have any suitable shape for securement around a user's extremity but preferably may be shaped as a wristband, wristwatch, bracelet, sleeve or similar structure. The first biometric monitoring device 200 may comprise a plurality of sensors 202 including, but not limited to, one or more of location tracking sensors, cameras, microphones, heart rate monitoring sensors, blood oxygen sensors, environmental and dermal temperature sensors, blood pressure sensors, device securement status sensors, accelerometers and any combination thereof. Further, the first biometric monitoring device 200 may comprise one or more processing devices 204 to read out one or more values associated with the plurality of sensors 202, an electronic display 206 to graphically display such values and a rechargeable power source 208 powering electronic components of the first biometric monitoring device 200.

The first biometric monitoring device 200 may further comprise a securement mechanism 210 for securing the device around a user's extremity such as a wrist, finger, arm, leg and the like. The securement mechanism 210 may take a form commensurate with the form taken by the device 200. For example, as shown in FIG. 2, the securement mechanism 210 may be a prong removably inserted into an aperture. Further, the mechanism 210 may be communicatively coupled to the one or more processing devices 204 to determine a securement status thereof.

The first biometric monitoring device 200 may monitor a plurality of parameters associated with a first user. The plurality of parameters may include, but are not limited to, one or more of first user location, live video feed, live audio feed, heart rate, blood oxygen level, temperature, blood pressure, device securement status and any combination thereof. Further, the first biometric monitoring device 200 may comprise one or more transceivers (not shown) for communicating values associated with the plurality of sensors 202 and parameters to the one or more remote devices 102. Any one or more of the plurality of parameters may be associated with one or more threshold values that trigger one or more events upon the given threshold value being met. The one or more events may include, but are not limited to, one or more of contacting emergency services, alerting one or more remote users in an audio, tactile and/or visual manner, alerting the first user in an audio, tactile and/or visual manner, alerting a second user in an audio, tactile and/or visual manner or any combination thereof.

The one or more remote devices 102 may comprise machine-readable memory storing software instructions that are executed by one or more processors to display a graphical user interface allowing for one or more remote users to interface with the first biometric device 200. For example, the one or more remote users may view the one or more values associated with the plurality of sensors 202 substantially in real-time. The one or more remote users may set and edit the threshold values associated with the plurality of parameters. The one or more remote users may set and edit the one or more events to be triggered upon the threshold values being met. The one or more remote users may unilaterally access any one or more of the plurality of sensors 202 and parameters associated with the first biometric monitoring device 200. The one or more remote users may contact the first user via text, audio and/or video communication between the remote device 102 and first biometric monitoring device 200 without the consent of the first user.

Further, the one or more remote users may have unilateral administrator access to one or more of the first user's past movements, present location, past and present audio and video feeds, past and present heart rate, past and present blood oxygen levels and the like. Additionally, the one or more remote users may be alerted via audio, tactile and/or video communication when the first user moves outside a threshold geofenced area, the first biometric monitoring device 200 is removed from the first user's extremity, the first user reads or acknowledges a communication from the one or more remote users, the accelerometer records a high-impact event or other of the one or more sensors 202 record a threshold-exceeding event.

While the first biometric device 200 is depicted in FIG. 2 as having a display screen, sensors, securement mechanism etc. with a particular shape, it is to be understood that the device 200 may not comprise a display screen, may have a variable number of sensors with varied shape and may comprise any suitable means of securing the device 200 to the first user's extremity including, but not limited to, magnets, hook and loop fasteners, snaps, buttons, fasteners, clasps, adhesives and the like.

Figure 3:
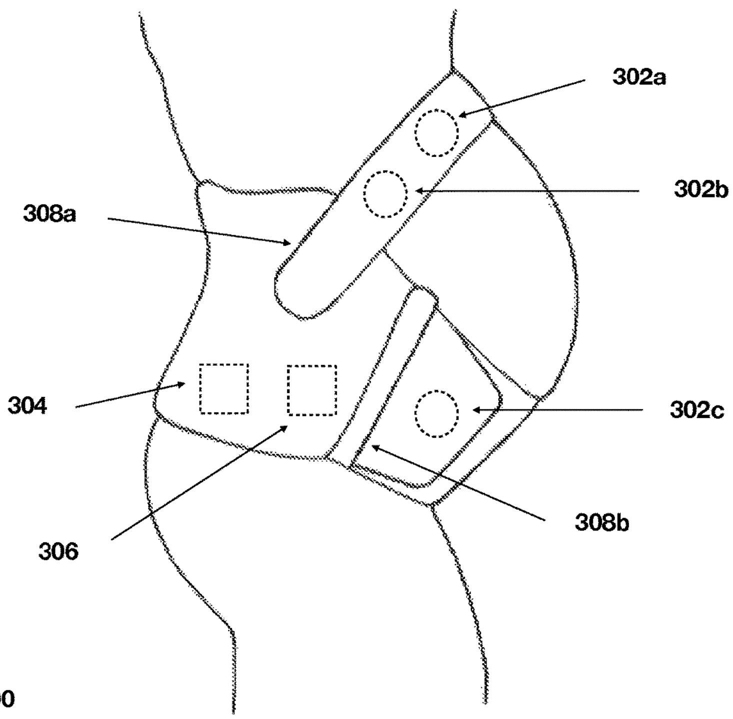
FIG. 3 is a detailed view of a second biometric monitoring device in accordance with some embodiments of the present invention.

As shown in FIG. 3, the second biometric monitoring device 300 may have any suitable shape for securement around a pregnant user's waist but preferably may be shaped as a brace, belt, band, sleeve or similar structure. The second biometric monitoring device 300 may comprise a plurality of sensors 302 including, but not limited to, one or more of ultrasound transceivers, heart rate monitoring sensors, blood oxygen sensors, dermal temperature sensors, blood pressure sensors, sweat analysis sensors, accelerometers and any combination thereof. Further, the second biometric monitoring device 300 may comprise one or more processing devices 304 to read out one or more values associated with the plurality of sensors 302 and a rechargeable power source 306 operating with a switch to be in an OFF state and an ON state for selectively powering electronic components of the second biometric monitoring device 300. Further, the one or more processing devices 304 may place the plurality of sensors 302 or the rechargeable power source 306 into an OFF state after predetermined period of time of user inactivity or irregardless of user activity to prevent electromagnetic exposure to a pregnant user's fetus.

The second biometric monitoring device 300 may further comprise one or more optional securement mechanisms 308 for securing the device around the pregnant user's waist including back, waist, womb, stomach and the like. The one or more optional securement mechanisms 308 may take a form commensurate with the form taken by the device 300. For example, as shown in FIG. 3, the one or more optional securement mechanisms 308 may be hook and loop fasteners disposed on surfaces thereof.

The second biometric monitoring device 300 may monitor a plurality of parameters associated with the pregnant user. The plurality of parameters may include, but are not limited to, one or more of fetal position, fetal orientation, heart rate, blood oxygen level, temperature, blood pressure, sweat composition and any combination thereof. One or more of these parameters may apply to the pregnant user and/or the pregnant user's fetus. Further, the second biometric monitoring device 300 may comprise one or more transceivers (not shown) for communicating values associated with the plurality of sensors 302 and parameters to the one or more remote devices 102. Any one or more of the plurality of parameters may be associated with one or more threshold values that trigger one or more events upon the given threshold value being met. The one or more events may include, but are not limited to, one or more of contacting emergency services, alerting one or more remote users in an audio, tactile and/or visual manner, alerting the first user in an audio, tactile and/or visual manner, alerting the pregnant user in an audio, tactile and/or visual manner or any combination thereof.

Further, the second user may have unilateral administrator access to one or more of the pregnant user's past fetal movements, present fetal location, past and present fetal orientation, past and present heart rate, past and present blood oxygen levels, past and present sweat analysis results and the like. One or more of these parameters may apply to the pregnant user and/or the pregnant user's fetus. Additionally, the one or more remote users may be alerted via audio, tactile and/or video communication when the pregnant user's fetus moves or orients itself outside a threshold position or orientation, the one or more parameters indicate that the pregnant user is about to go into labor, the pregnant user or their fetus is experiencing malnutrition, the pregnant user's fetus is not receiving enough oxygen, the accelerometer records a high-impact event or other of the one or more sensors 302 record a threshold-exceeding event.

While the second biometric device 300 is depicted in FIG. 3 as having a generally cylindrical body shape, a plurality of sensors, a plurality of securement mechanisms etc. with a particular shape, it is to be understood that the device 300 may comprise an altered but similar body shape, may have a variable number of sensors with varied shape and may comprise any suitable means of securing the device 300 to the pregnant user's extremity including, but not limited to, magnets, hook and loop fasteners, snaps, buttons, fasteners, clasps, adhesives and the like. Further, the over belly strap shown terminating at securement mechanism 308*a* may be optionally included and is intended to offer another portion for installation of sensors 302 and additionally to offer mechanical support to the pregnant user's back and womb.

Figure 4:
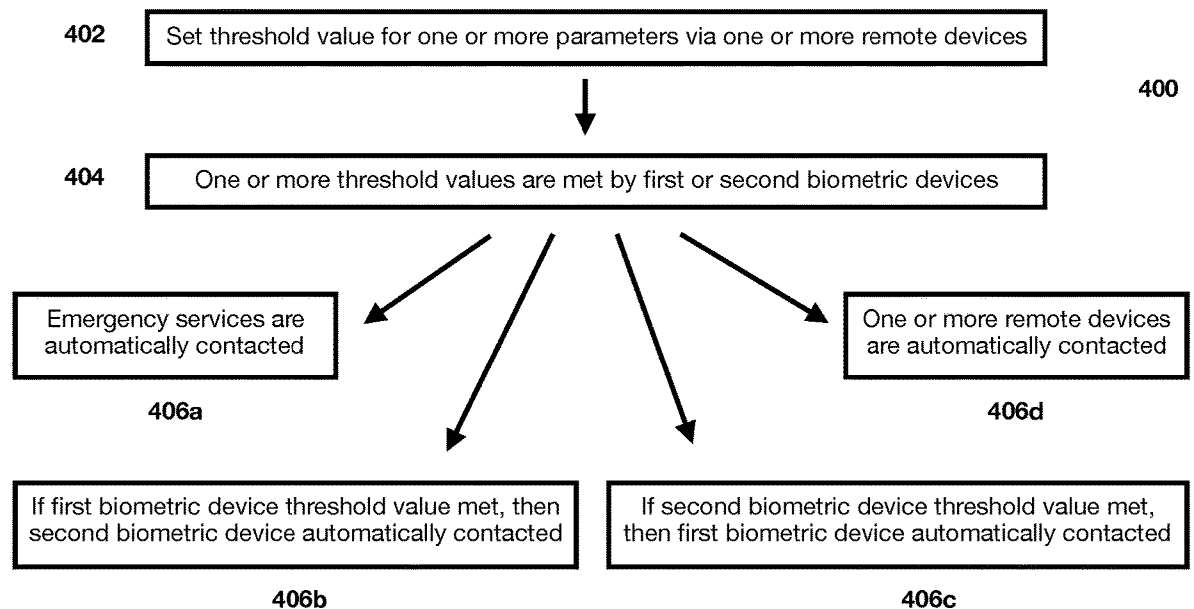
FIG. 4 is a flow chart of a method of operating a biometric monitoring system in accordance with some embodiments of the present invention.

As shown in FIG. 4, a method 400 may utilize the remote electronic devices 102, first biometric monitoring device 104 and second biometric monitoring device 106 of FIG. 1 to, in step 402, set one or more threshold values for one or more parameters for the first or second biometric monitoring devices 104, 106 by the one or more remote users utilizing the remote electronic devices 102. In one embodiment, the one or more remote users may include the pregnant user. In step 404, the first or second biometric monitoring devices 104, 106 determine that the one or more threshold values have been met. In response to determining that the one or more threshold values have been met, one or more of the following actions may be substantially simultaneously taken: automatically contacting emergency services, automatically contacting the pregnant user's biometric monitoring device, automatically contacting the first user's biometric device, automatically contacting the one or more remote devices 102. In some embodiments, the one or more remote devices 102 may be operated by the first user, pregnant user, remote user or combinations thereof. The action of automatically contacting may comprise an audio, tactile and/or visual communication.

Each of the the remote electronic devices, first biometric monitoring device and second biometric monitoring device may utilize one or more transceivers that may wirelessly communicate over any suitable communications protocol including, but not limited to, WiFi, cellular data networks, satellite, Bluetooth, near-field communication and the like. Further, the rechargeable power sources of the biometric monitoring devices may comprise a compatible charging port by which the power sources may be recharged. Additionally, the materials utilized in manufacturing the first and second biometric monitoring devices may be non-limiting and may comprise any suitable flexible material including any plastic polymer, nylon, polyester, cotton, rayon and the like.

Those of skill in the art will recognize many modifications may be made to this configuration without departing from the scope, spirit or intent of the claimed subject matter. Furthermore, the disclosed subject matter may be implemented as a system, method, apparatus, or article of manufacture using standard programming and engineering techniques to produce software, firmware, hardware, or any combination thereof to control a computer or processor-based device to implement aspects detailed herein.

Also, techniques, systems, subsystems and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component, whether electrically, mechanically, or otherwise. Other examples of changes, substitutions, and alterations are ascertainable by one skilled in the art and may be made without departing from the spirit and scope disclosed herein. Although the present invention has been described in detail, it should be understood that various changes, substitutions and alterations can be made hereto without departing from the spirit and scope of the invention as defined by the appended claims.

The invention claimed is:

1. A biometric monitoring system, comprising:

one or more first biometric monitoring devices each comprising a first plurality of biometric sensors, a display screen, a first band body and a first securement mechanism coupling the first band body around a first user's body part, wherein the first band body and display screen structurally support the first plurality of biometric sensors and wherein the first band body comprises an annular shape; and a second biometric monitoring device comprising a second plurality of biometric sensors, a second band body and a second securement mechanism coupling the second band body around a pregnant user's back, sides and midriff, wherein the second band body structurally supports one or more of the second plurality of biometric sensors and wherein the second band body comprises an annular shape having a vertical height reaching a maximum at the pregnant user's back and tapering to a minimum at the pregnant user's midriff, wherein the one or more first biometric monitoring devices are in wireless communication with one or more remote electronic devices and the one or more second biometric monitoring devices, and the one or more second biometric monitoring devices are in wireless communication with the one or more remote electronic devices, wherein the one or more remote electronic devices each comprise a graphical user interface allowing a remote user to set one or more threshold values for each of the first and second plurality of biometric sensors such that, when the first or second biometric monitoring devices determine that the one or more threshold values have been met, two or more actions are triggered, wherein the two or more actions triggered comprise alerting emergency services, alerting the first user, alerting the pregnant user and alerting the one or more remote users, wherein the alerting is performed in real-time via two or more of audio communication, tactile communication and video communication.

2. The biometric monitoring system of claim 1, wherein the first plurality of biometric sensors comprise two or more selected from the group consisting of: location tracking sensors, cameras, microphones, heart rate monitoring sensors, blood oxygen sensors, environmental and dermal temperature sensors, blood pressure sensors, securement mechanism status sensors, accelerometers and any combination thereof.

3. The biometric monitoring system of claim 2, wherein the first plurality of biometric sensors monitor in real-time two or more parameters selected from the group consisting of: first user location, live video feed, live audio feed, heart rate, blood oxygen level, temperature, blood pressure, securement mechanism status, acceleration and any combination thereof.

4. The biometric monitoring system of claim 1, wherein the second plurality of biometric sensors comprise two or more selected from the group consisting of: ultrasound transceivers, heart rate monitoring sensors, blood oxygen sensors, dermal temperature sensors, blood pressure sensors, sweat analysis sensors, accelerometers and any combination thereof.

5. The biometric monitoring system of claim 1, wherein the second plurality of biometric sensors monitor in real-time two or more parameters selected from the group consisting of: fetal position, fetal orientation, heart rate, blood oxygen level, temperature, blood pressure, sweat composition, acceleration and any combination thereof.

6. The biometric monitoring system of claim 1, wherein the one or more threshold values determine any one of the following: when a fetus of the pregnant user moves or orients itself outside a threshold position or orientation, when the pregnant user is starting labor, when the pregnant user or their fetus is experiencing malnutrition, when the fetus of the pregnant user is not receiving enough oxygen, when an accelerometer records a high-impact event or any combination thereof.

7. The biometric monitoring system of claim 1, wherein the second biometric monitoring device comprises a third band body coupled to the second band body at two locations such that the third band body forms an acute angle with the second band body at each of the two locations of at least 45 degrees in a plane parallel an exterior dermal surface of the pregnant user's womb.

8. The biometric monitoring system of claim 7, wherein the two locations are disposed adjacent the pregnant user's womb.

9. The biometric monitoring system of claim 8, wherein the third band body is disposed over a top of the pregnant user's womb.

10. The biometric monitoring system of claim 1, wherein the second biometric monitoring device comprises a rechargeable power source operably coupled to a switch configured to selectively place the second biometric monitoring device in an ON state and an OFF state.

11. The biometric monitoring system of claim 10, wherein the rechargeable power source is operably coupled to a processing control unit configured to place the switch into the OFF state after a predetermined period of time of inactivity.

12. The biometric monitoring system of claim 1, wherein the second biometric monitoring device comprises one or more processing control units configured to selectively place one or more of the second plurality of biometric sensors in an ON state and an OFF state.

13. The biometric monitoring system of claim 12, wherein the one or more processing control units place one or more of the second plurality of biometric sensors into the OFF state after a predetermined period of time of inactivity.

14. A biometric monitoring system, comprising:

one or more first biometric monitoring devices each comprising a first plurality of biometric sensors, a display screen, a first band body and a first securement mechanism coupling the first band body around a first user's body part, wherein the first band body comprises an annular shape; and a second biometric monitoring device comprising a second plurality of biometric sensors, a second band body and a second securement mechanism coupling the second band body around a pregnant user's back, sides and midriff, wherein the second band body structurally supports one or more of the second plurality of biometric sensors and wherein the second band body comprises an annular shape having a vertical height reaching a maximum at the pregnant user's back and tapering to a minimum at the pregnant user's midriff, wherein the second biometric monitoring device comprises a third band body disposed over a top of the pregnant user's womb and coupled to the second band body at two locations adjacent opposite sides of the pregnant user's womb such that the third band body forms an acute angle with the second band body at each of the two locations of at least 45 degrees in a plane parallel an exterior dermal surface of the pregnant user's womb, wherein the second plurality of biometric sensors comprise at least one ultrasound transceiver, at least one heart rate monitoring sensor, at least one blood oxygen sensor, at least one dermal temperature sensor, at least one blood pressure sensor, at least one sweat analysis sensor and at least one accelerometer, wherein the second biometric monitoring device comprises one or more processing control units configured to selectively place one or more of the second plurality of biometric sensors in an ON state and an OFF state and wherein the one or more processing control units place one or more of the second plurality of biometric sensors into the OFF state after a predetermined period of time irregardless of the pregnant user's activity to prevent electromagnetic exposure to a pregnant user's fetus, wherein the one or more first biometric monitoring devices are in wireless communication with one or more remote electronic devices and the one or more second biometric monitoring devices, and the one or more second biometric monitoring devices are in wireless communication with the one or more remote electronic devices, wherein the one or more remote electronic devices each comprising a graphical user interface allowing a remote user to set one or more threshold values for each of the first and second plurality of biometric sensors such that, when the first or second biometric monitoring devices determine that the one or more threshold values have been met, two or more actions are triggered, wherein the two or more actions triggered comprise alerting emergency services, alerting the first user, alerting the pregnant user and alerting the one or more remote users, wherein the alerting is performed in real-time via two or more of audio communication, tactile communication and video communication.

15. The biometric monitoring system of claim 14, wherein the first plurality of biometric sensors comprise two or more selected from the group consisting of: location tracking sensors, cameras, microphones, heart rate monitoring sensors, blood oxygen sensors, environmental and dermal temperature sensors, blood pressure sensors, securement mechanism status sensors, accelerometers and any combination thereof.

16. The biometric monitoring system of claim 14, wherein the one or more threshold values determine any one of the following: when the fetus of the pregnant user moves or orients itself outside a threshold position or orientation, when the pregnant user is starting labor, when the pregnant user or their fetus is experiencing malnutrition, when the fetus of the pregnant user is not receiving enough oxygen, when an accelerometer records a high-impact event or any combination thereof.

17. A computer-implemented method of operating a biometric monitoring system comprising one or more processing control units executing software stored in machine-readable memory to perform actions comprising:

communicating electronic data between one or more first biometric monitoring devices, a second biometric monitoring device and one or more remote electronic devices, wherein the one or more first biometric monitoring devices each comprising a first plurality of biometric sensors, a display screen, a first band body and a first securement mechanism coupling the first band body around a first user's body part, wherein the first band body comprises an annular shape, wherein the second biometric monitoring device comprising a second plurality of biometric sensors, a second band body and a second securement mechanism coupling the second band body around a pregnant user's back, sides and midriff, wherein the second band body structurally supports one or more of the second plurality of biometric sensors and wherein the second band body comprises an annular shape having a vertical height reaching a maximum at the pregnant user's back and tapering to a minimum at the pregnant user's midriff, wherein the second biometric monitoring device comprises a third band body disposed over a top of the pregnant user's womb and coupled to the second band body at two locations adjacent opposite sides of the pregnant user's womb such that the third band body forms an acute angle with the second band body at each of the two locations of at least 45 degrees in a plane parallel an exterior dermal surface of the pregnant user's womb, wherein the second plurality of biometric sensors comprise at least one ultrasound transceiver, at least one heart rate monitoring sensor, at least one blood oxygen sensor, at least one dermal temperature sensor, at least one blood pressure sensor, at least one sweat analysis sensor and at least one accelerometer;

setting, via a graphical user interface of the one or more remote electronic devices, a plurality of threshold values associated with the first and second plurality of biometric sensors;

iteratively comparing the plurality of threshold values against a plurality of parameters measured by the first and second plurality of biometric sensors; and determining whether the plurality of parameters meet or exceed the plurality of threshold values, wherein, in response to determining that the plurality of threshold values have been met or exceeded, two or more actions occur, wherein the two or more actions triggered comprise alerting emergency services, alerting the first user, alerting the pregnant user and alerting the one or more remote users, wherein the alerting is performed in real-time via two or more of audio communication, tactile communication and video communication.

18. The computer-implemented method of claim 17, wherein the first plurality of biometric sensors comprise two or more selected from the group consisting of: location tracking sensors, cameras, microphones, heart rate monitoring sensors, blood oxygen sensors, environmental and dermal temperature sensors, blood pressure sensors, securement mechanism status sensors, accelerometers and any combination thereof.

* * * * *